(12) United States Patent
Nair et al.

(10) Patent No.: US 8,470,147 B2
(45) Date of Patent: Jun. 25, 2013

(54) CO-FIRED GAS SENSOR

(75) Inventors: Balakrishnan G. Nair, Sandy, UT (US); Jesse Nachlas, Salt Lake City, UT (US); Gangqiang Wang, Salt Lake City, UT (US)

(73) Assignee: Caterpillar Inc., Peoria, IL (US)

( * ) Notice: Subject to any disclaimer, the term of this patent is extended or adjusted under 35 U.S.C. 154(b) by 922 days.

(21) Appl. No.: 12/155,167

(22) Filed: May 30, 2008

(65) Prior Publication Data

US 2009/0294285 A1   Dec. 3, 2009

(51) Int. Cl.
*G01N 27/409* (2006.01)

(52) U.S. Cl.
USPC ............ 204/426; 204/431; 204/424; 205/785

(58) Field of Classification Search
USPC ... 204/421–429; 205/781, 784, 785; 73/23.31
See application file for complete search history.

(56) References Cited

U.S. PATENT DOCUMENTS

| | | | |
|---|---|---|---|
| 5,989,398 A | 11/1999 | Young et al. | |
| 6,136,170 A | 10/2000 | Inoue et al. | |
| 6,723,217 B1 | 4/2004 | Duce et al. | |
| 7,217,355 B2 | 5/2007 | Nair et al. | |
| 7,279,133 B2 | 10/2007 | Chen et al. | |
| 2002/0100697 A1 | 8/2002 | Quinn et al. | |
| 2002/0108855 A1* | 8/2002 | Wang et al. | 204/425 |
| 2002/0108871 A1 | 8/2002 | Wang et al. | |
| 2002/0108872 A1 | 8/2002 | Symons et al. | |
| 2002/0134487 A1 | 9/2002 | Polikarpus et al. | |
| 2003/0159928 A1 | 8/2003 | Kojima et al. | |
| 2003/0221975 A1 | 12/2003 | Mizutani et al. | |
| 2004/0026268 A1 | 2/2004 | Maki et al. | |
| 2004/0094416 A1 | 5/2004 | Chen et al. | |
| 2004/0226832 A1 | 11/2004 | Jain et al. | |
| 2007/0012566 A1 | 1/2007 | Nair et al. | |
| 2007/0125647 A1 | 6/2007 | Wang et al. | |
| 2007/0246360 A1 | 10/2007 | Schneider et al. | |

\* cited by examiner

*Primary Examiner* — Keith Hendricks
*Assistant Examiner* — Kourtney S Carlson
(74) *Attorney, Agent, or Firm* — Finnegan, Henderson, Farabow, Garrett & Dunner LLP

(57) ABSTRACT

A sensor for detecting a gas is provided. The gas sensor may have a sensing section, a heating section, and a resistance temperature detector. The resistance temperature detector may be co-fired to be integral with at least one of the sensing section and the heating section.

5 Claims, 2 Drawing Sheets

CO-FIRED GAS SENSOR

TECHNICAL FIELD

The present disclosure relates generally to a gas sensor and, more particularly, to a co-fired gas sensor with an integral resistance temperature detector (RTD), and methods of making the gas sensor.

BACKGROUND

The composition of exhaust produced by the combustion of hydrocarbon fuels is a complex mixture of oxide gases ($NO_x$, $SO_x$, $CO_2$, CO, $H_2O$), unburned hydrocarbons, and oxygen. Measurement of the concentration of these individual exhaust gas constituents in real time can be used to improve combustion efficiency and lower emissions of polluting gases. Various devices have been proposed to operate as exhaust gas sensors that have the capability of measuring the concentration of a constituent within an exhaust stream.

One gas sensor known in the art is configured as a flat plate multilayer ceramic package designed to include a sensing component and a heating component. The sensing component includes one or more electrodes (e.g., a reference electrode and a sensing electrode) disposed on opposing sides of an electrolyte substrate. The heating component includes a heating element bonded to an electrically insulating substrate. The sensing component and the heating component are shaped from green sheets of the electrolyte and insulating materials (typically zirconia and alumina), respectively, which are stacked together and then sintered to bond the two components.

During operation of the sensor, the heating component is energized to raise the temperature of the sensing component to within an optimum operational range. When the temperature of the sensing component is within this range, the sensing component may be sufficiently accurate at detecting the presence of a particular exhaust constituent. However, when outside of the temperature range, signals generated by the sensing component may be unreliable. Unfortunately, it can be difficult to accurately control operation of the heater such that the temperature of the sensing component remains within the optimum operational range.

One way to improve heater control is disclosed in US Patent Application Publication No. 2007/0125647 (the '647 publication) by Wang et al. published Jun. 7, 2007. Specifically, the '647 publication discloses a sensor having a sensing element configured to detect an exhaust gas species such as NOx, and a heater co-fired with the sensing element. An RTD is glass bonded to the heater side of the already sintered sensor for use in sensing and controlling a temperature of the heater. Based on a current or voltage signal from the RTD indicative of a temperature of the heater, a current applied to the heater is varied so as to maintain the sensing element at a desired temperature.

Although perhaps an improvement over previous sensors that did not include an RTD, the gas sensor of the '647 publication may be expensive and still have reduced reliability and applicability. That is, because the RTD is glass bonded to an already sintered sensor, an extra assembly step is required that may increase assembly cost and assembly time. In addition, the glass bond may be prone to cracking when exposed to temperature gradients or extreme temperatures. And, as the RTD can only be placed outward of the heater when bonded separately, readings of the RTD may not accurately reflect the actual temperatures experienced by the sensing element.

The disclosed gas sensors are directed at solving one or more of the problems set forth above.

SUMMARY OF THE DISCLOSURE

In one aspect, the present disclosure is directed to a gas sensor. The gas sensor may include a sensing section, a heating section, and a resistance temperature detector. The resistance temperature detector may be co-fired to be integral with at least one of the sensing section and the heating section.

In yet another aspect, the present disclosure is directed to a method of fabricating a gas sensor. The method may include preparing a green electrolyte substrate, and connecting at least one sensing electrode to the green electrolyte substrate. The method may further include preparing a first green insulating substrate, and connecting a heating element to the first green insulating substrate. The method may also include preparing a second green insulating substrate, and connecting a resistance temperature detector to the second green insulating substrate. The method may additionally include co-firing the green electrolyte substrate together with at least one of the first and second green insulating substrates.

In a further aspect, the present disclosure is directed to a gas sensor. The gas sensor includes an ionically conductive substrate, and a sensing electrode and a reference electrode coupled to opposite sides of the ionically conductive substrate and configured to detect a gaseous chemical species. The gas sensor also includes a first electrically insulating substrate, a heating coil attached to the first electrically insulating substrate, and a second electrically insulating substrate. The gas sensor further includes a resistance temperature detector attached to the second electrically insulating substrate. The ionically conductive substrate, the first electrically insulating substrate, and the second electrically insulating substrate are co-fired to form a single integral component, and a coefficient of thermal expansion of the second electrically insulating substrates is within about 1 ppm/° C. of coefficients of thermal expansion of the ionically conductive substrate and the first electrically insulating substrate.

DETAILED DESCRIPTION

Figure 1:
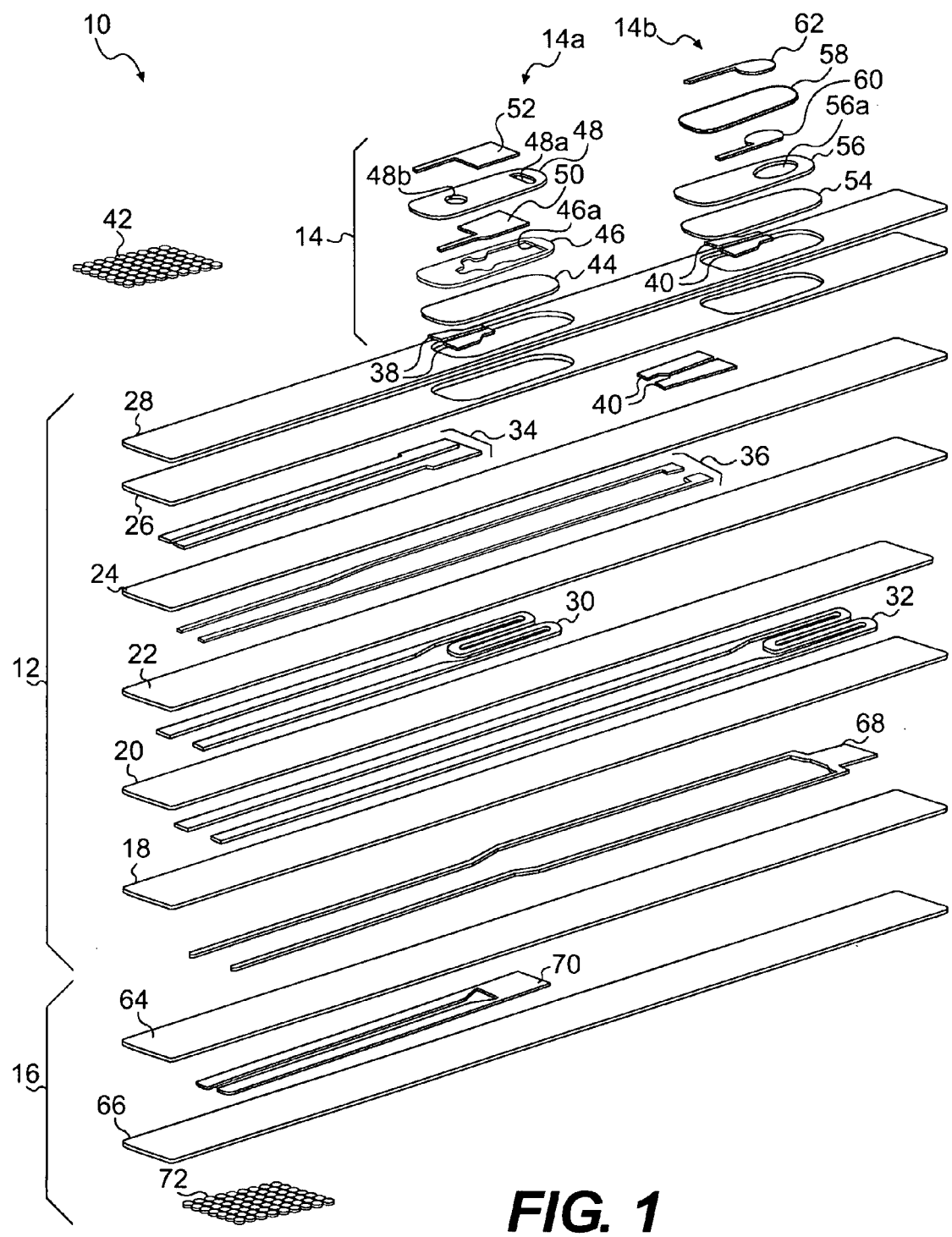
FIG. 1 is an exploded view illustration of an exemplary disclosed sensing assembly.

Referring to FIG. 1, the basic features of a gas sensor 10 are illustrated. Sensor 10 may include multiple sections that perform different functions, including a heating section 12, a gas sensing section 14, and a temperature sensing section 16. In the embodiment of FIG. 1, the sections of sensor 10 may cooperate to separately sense the presence of two different constituents, for example $NO_x$ and $O_2$, within the same exhaust stream. However, different embodiments of sensor 10 may be configured to sense any number and type of gaseous constituent.

Heating section 12 is shown in FIG. 1 as having multiple layers. Specifically, sensor 10 is depicted in an exploded view such that individual layers 18, 20, 22, 24, 26 and 28 that make up heating section 12 are shown to overlap as they would in a fully assembled sensor 10. This view illustrates the relationship between features of heating section 12, as well as features of gas sensing section 14 and temperature sensing section 16.

Layers 18-28 may generally embody electrically insulating (electrically non-conductive) regions of heating section 12. A variety of ceramic materials are known in the art that could be used for constructing the insulating regions, as would be understood by one of ordinary skill in the art. In one example, the insulating ceramic material may be primarily composed of a spinel material such as magnesium aluminate spinel. In another example, the insulating ceramic material may be primarily composed of alumina. To produce layers 18-28, the insulating material may be mixed with binders, solvents, and/or plasticizers and formed into a slurry, which may be tape cast and dried prior to further manufacturing steps, such as sintering. Segments of the dried tape may be cut to desired shapes using techniques common in the art. These techniques could include, but are not limited to, punching and laser machining.

Before sintering of the green tape, additional elements may be included in (i.e., bonded to, embedded within, printed, or otherwise joined to) the dried tape of some or all of layers 18-28. Specifically, one or more heating elements may be included in layer 20, while one or more electrical leads may be included in layer 24. A variety of methods known in the art, such as, for example, screen printing, may be utilized to include the heating elements (30 and 32), and electrical leads (34 and 36) in the layers. In the embodiment of FIG. 1, two separate heating elements 30 and 32 may be printed on opposite sides of layer 20, and two separate sets of power/signal leads 34, 36 may be printed on opposite sides of layer 24. In some embodiments, elements may be included only on one side of a layer. For instance, in the embodiment of FIG. 1, lead 34 may be printed on layer 24, lead 36 may be printed on layer 22, heating element 30 may be printed on layer 20, and heating element 32 may be printed on layer 18.

Heating element 30 may be configured to warm a first sensing component 14a of gas sensing section 14. Specifically, first sensing component 14a may be a $NO_x$ sensing component that functions optimally when exposed to operating temperatures between about 300° C.-600° C. and, more preferably, temperatures between about 450° C.-550° C. To facilitate operation of first sensing component 14a, heating element 30 may, through resistance heating, create a first temperature zone in the general area of first sensing component 14a (i.e., relative to a length direction of sensor 10). Heating element 30 may include a metallic coil that may be screen printed on layer 20. A coil length and a cross-sectional area of heating element 30 may affect a temperature of first temperature zone. Heating element 30 may be designed to accommodate a supply of power in the range of about 9-24 volts and, more specifically, in the range of about 12-18 volts.

Heating element 32 may be configured to warm a second sensing component 14b of gas sensing section 14. Specifically, second sensing component 14b may be an $O_2$ sensing component that functions optimally when exposed to operating temperatures of about 500° C.-900° C. and, more preferably, temperatures of about 650° C.-750° C. To facilitate operation of second sensing component 14b, heating element 32 may, through resistance heating, create a second temperature zone in the general area of second sensing component 14b (i.e., relative to the length direction of sensor 10). Heating element 32, like heating element 30, may embody a metallic coil applied as an ink through screen printing to layer 18 (or to a side of layer 20 opposite the side where heating element 30 may be printed), wherein a coil length and/or a cross-sectional area of heating element 32 may affect a temperature of second sensing component 14b. Heating element 32 may also be designed to accommodate a supply of power in the range of about 9-24 volts and, more specifically, in the range of about 12-18 volts.

Heating elements 30, 32 may be located such that the resulting temperature zones may be substantially isolated from each other (i.e., such that one heating zone does not substantially affect a temperature of the other heating zone). That is, in addition to being located on opposing sides of layer 20, heating elements 30, 32 may also be spaced apart in a length direction of sensor 10. Thus even though heating elements 30 and 32 may be substantially aligned in a width direction of sensor 10, the spacing in the length direction may help to thermally isolate the two temperature zones from each other. Alternatively, heating elements 30, 32 may be located adjacent to or nested within each other, if desired.

Electrical leads 34 and 36 may be configured to transfer electrical signals from first and second sensing components 14a and 14b to an electronic control module. Electrical leads 34 may form a continuous electrical path with first sensor 14a by way of contacts 38 and vias (not shown) through layer 26. A via may be a hole or a cavity through a layer that may be lined or filled with a conductive material to transmit electrical signals through the layer. For instance, the via through layer 26 may maintain electrical connectivity between contact 38 and electrical lead 34 through layer 26. Similarly, electrical leads 36 may form a continuous electrical path with second sensor 14b by way of contacts 40 and vias (not shown) through layer 24.

A terminal contact pad 42 may be located on an external surface of layer 28 to connect heating elements 30, 32 and electrical leads 34, 36 to desired instrumentation (for instance, power supply, electronic control module, on-board computer, emission control system, etc.). Terminal contact pad 42 may include multiple electrical terminals that may be electrically coupled to heating elements 30, 32 and electrical leads 34, 36. The multiple electrical terminals of terminal contact pad 42 may connect to heating elements 30, 32 and to electrical leads 34, 36 by way of vias (not shown) through layers 20, 24, 26, and 28. Although FIG. 1 depicts all the electrical terminals that form terminal contact pad 42 to be clustered together at one location, it is contemplated that, in some embodiments, electrical terminals of terminal contact pad 42 may be positioned at different locations. For instance, the terminals that are electrically coupled to the heating elements (30 and 32) may be clustered together at one location, while the terminals that are electrically coupled to electrical leads 34 and 36 may be clustered together at another location. By way of another example, the terminals electrically coupled to a heating element and a corresponding sensor (that is, for example, terminals electrically coupled to heating element 30 and electrical lead 34) may be positioned at one location, while the terminals electrically coupled to another heating element and a corresponsing sensor may be located at a different location.

Similar to heating component 12, first sensing component 14a may have multiple layers. Specifically, first sensing component 14a may include three layers 44, 46, and 48. Layers 44-48 may generally embody ionically conductive regions of first sensing component 14a. A variety of ionically conductive electrolyte materials are known in the art that could be used for constructing the conductive regions, as would be understood by one of ordinary skill in the art. In one example, the electrolyte ceramic material is a zirconia based material, for example yttria stabilized zirconia (YSZ). To produce layers 44-48, the YSZ may be mixed with binders, solvents, and plasticizers and formed into a slurry, which may be tape cast and dried prior to further manufacturing steps. Segments of the dried tape may be cut to approximate shape using techniques common in the art.

Before sintering of the green YSZ tape, additional elements may be included in (i.e., bonded to, embedded within, or otherwise joined to) the dried tape of layers 44 and 48. Specifically, one or more sensing electrodes fabricated from, for example, Pt (platinum) or $WO_3/ZrO_2$ (tungsten oxide/zirconium oxide), may be connected to layer 48, while contacts 38 may be connected to an external surface of layer 44. In one example, a reference electrode 50 may be connected to an internal surface of layer 48, while a $NO_x$ sensing electrode 52 may be connected to an external surface of layer 48. Electrical connections between contacts 38 and electrodes 50, 52 may be facilitated by way of vias (not shown) through layers 44-48. A variety of methods known in the art may be utilized to connect contacts 38 and electrodes 50, 52 to layers 44 and 48, respectively. In one example, screen printing may be utilized.

Reference electrode 50 may be associated with an open reference chamber, which may be formed by layers 44-48, and in communication with reference electrode 50 when first sensing component 14 is fully assembled. Specifically, layer 46 may include a centralized cavity 46a that, when sandwiched between layers 44 and 48, forms the open reference chamber. A first and a second opening 48a, 48b in layer 48 may communicate a flow of exhaust gas with the reference chamber and with reference electrode 50 located therein. In some embodiments, instead of an open reference chamber, a closed reference chamber having reference gas (for example, air) trapped therein may be utilized, if desired.

Second sensing component 14b may also have multiple layers. Specifically, second sensing component 14b may include three layers 54, 56, and 58. Layers 54-58 may generally embody electrically conductive regions of second sensing component 14b. A variety of electrolyte materials are known in the art that could be used for constructing the conductive regions, as would be understood by one of ordinary skill in the art. In one example the electrolyte ceramic material is YSZ. To produce layers 54-58, the YSZ may be formed into a slurry, which may be tape cast and dried prior to further manufacturing steps. Segments of the dried tape may be cut to approximate shape using techniques common in the art.

Before sintering of the green YSZ tape, additional elements may be connected (i.e., bonded to, embedded within, or otherwise joined to) the dried tape of layers 54 and 58. Specifically, one or more sensing electrodes fabricated from, for example, platinum, may be connected to layer 58, while contacts 40 may be connected to an external surface of layer 54. In one example, a reference electrode 60 may be connected to an internal surface of layer 58, while an $O_2$ sensing electrode 62 may be connected to an external surface of layer 58. Electrical connections between contacts 40 and electrodes 60, 62 may be facilitated by way of vias (not shown) through layers 54-58. A variety of methods known in the art may be utilized to connect contacts 40 and electrodes 60, 62 to layers 54 and 58, respectively. In one example, screen printing may be utilized.

Reference electrode 60 may be associated with a closed reference chamber, which may be formed by layers 54-58 when second sensing component 14b is fully assembled. Specifically, layer 56 may include a centralized cavity 56a that, when sandwiched between layers 54 and 58, forms the reference chamber. Air trapped within the reference chamber during manufacture of sensor 10 may serve as a reference gas for second sensing component 14b. It is contemplated that, instead of a closed reference chamber, a reference chamber open to the atmosphere or a chamber that includes an equilibrium electrode or structure such as a metal/metal-oxide mixture may be utilized, if desired.

Temperature sensing section 16 may embody a multi-layer structure configured to sense the temperature zones created by first and second heating elements 30, 32. Specifically, temperature sensing section 16 may include two layers 64 and 66 (one layer for each temperature zone). Layers 64 and 66 may generally embody electrically insulating regions of temperature sensing section 16. A variety of ceramic materials are known the art that could be used for constructing the insulating regions, as would be understood by one of ordinary skill in the art. In one example, the insulating regions of temperature sensing section 16 may be fabricated from the same material as the insulating regions of heating section 12, for example, from a spinel-containing material (such as, for example, magnesium aluminate spinel). In another embodiment, the insulating regions of temperature sensing section 16 may be fabricated from a material having substantially the same coefficient of thermal expansion (CTE) as the insulating material of the heating section 12 (spinel material) and the electrolyte material of the gas sensing section 14 (YSZ). In this disclosure, two materials are considered to have substantially the same CTE, if the CTEs of the two materials at any temperature, in the temperature range of 22-900° C., is within about 1 ppm/° C. In one specific example, the coefficient of thermal expansion of the insulating region of the temperature sensing section 16 may be between the coefficients of thermal expansion of spinel and YSZ. To produce layers 64, 66, the insulating material may be mixed with binders, solvents, and/or plasticizers and formed into a slurry, which may be tape cast and dried prior to further manufacturing steps. Segments of the dried tape may be cut to approximate shape using techniques common in the art.

Before sintering of the green tape, additional elements may be connected to (i.e., bonded to, embedded within, or otherwise joined to) the dried tape of layers 64 and 66. Specifically, one or more resistance temperature detectors (RTDs) may be connected to layers 64 and 66. In the embodiment of FIG. 1, two separate RTDs 68 and 70 may be connected to layers 64 and 66, respectively. Although illustrated as being connected to separate layers 64 and 66, it is contemplated that the separate RTDs may alternatively be connected to only a single layer, if desired. A variety of methods known in the art may be utilized to connect RTDs to layers 64 and 66. For example, screen printing may be utilized.

For the purposes of this disclosure, an RTD may be defined as a component used to measure a temperature of a heating zone (i.e., of first or second sensing components 14a or 14, of first or second heating elements 30, 32, or the areas therebetween) within sensor 10 by correlating a measured resistance of the RTD with a temperature value. In one example, the RTD may include a screen printed coil made from a material with known resistance values indexed to a range of temperatures. Thus, based on a measured resistance of the RTD, a temperature of the associated heating zone may be estimated by referencing the index. RTDs are typically fabricated from platinum, although other materials may also be utilized.

RTDs 68 and 70 may be associated with particular heating zones of sensor 10. Specifically, RTD 68 may be generally located proximate heating element 32 (relative to a length direction of sensor 10) to sense the temperature of the second heating zone, while RTD 70 may be generally located proximal heating element 30 to sense the temperature of the first heating zone. As a result, the temperature measured by RTD 68 may be generally associated with second sensing component 14b, while the temperature measured by RTD 70 may be generally associated with first sensing component 14a.

A terminal contact pad 72 may be located on an external surface of layer 66 (or another layer located outward of layer 66) to connect an external power supply (not shown) to RTDs 68, 70 and/or heating elements 30, 32. Similar to terminal contact pad 42, terminals of terminal contact pad 72 may connect to RTDs 68, 70 and/or heating elements 30, 32 by way vias (not shown) through layers 64, 66, 18 and 20. As with terminal contact pad 42, different configurations of the terminals of terminal contact pad 72 are contemplated. In some embodiments, terminal contact pad 72 may be combined with terminal contact pad 42.

The different sections of sensor 10 may be co-fired to produce a single integral unit. That is, after connecting some or all of the elements to the different green layers, the green layers may be stacked together and laminated using a technique such as solvent bonding, pressure/heat lamination, or another technique known to one of ordinary skill in the art. In methods using pressure/heat lamination, the individual green layers are pressed together using a lamination press. Any internal elements (e.g., electrodes, contacts, heater coils, RTDs, etc.) may be screen printed or otherwise applied to the green ceramic tape prior to lamination. After lamination, sensor 10 may be cut to final shape using techniques known to those of ordinary skill in the art, and then sintered for about two hours at a temperature of about 1500° C. Following sintering, external elements may be applied to the sintered components. For example, the side of first sensing component 14a corresponding with layer 52 may be coated with an electrode material containing a metal or a metal oxide to make up $NO_x$ sensing electrode 52. $NO_x$ sensing electrode 52 may be preferably placed on first sensing component 14a after sintering to prevent excessive densification of the sensing electrode or high-temperature chemical reaction with YSZ in the green tape. Similarly, second sensing component 14b may be coated with platinum for oxygen sensing electrode 62 on the side corresponding to layer 58. The sensing components (first sensing component 14a and second sensing component 14b) may be fired at a temperature between about 600-1200° C. to cure the electrodes and promote adhesion of the electrodes to YSZ. It is contemplated that terminal contact pads 42 and/or 72 may also be applied to sensor 10 during this process stage, if desired.

It is contemplated that, rather than co-firing, heating, gas sensing, and temperature sensing sections 12-16, gas sensing section 14 could be separately sintered, if desired. In this situation, after sintering, first and second sensing components 14a, b may be received within recesses of and bonded to heating section 12. To bond first and second sensing components 14a, b to heating section 12, a bonding paste or ink may be applied to the interface (i.e., to the internal surface of heating section 12 and/or to the internal surfaces of first and second sensing components 14a,b). The paste may be fabricated from a bond material having a firing temperature lower than the sintering temperature of either the electrolyte material or the insulating material. The bond material may also have a CTE substantially matched to the CTEs of both the electrolyte material and the insulating material. In one example, the bond material may be a glass, for example commercially available E2 or S2 glass. In another example, the bond material may be a pliable metal, for example silver. After application of the bond material, first and second sensing components 14a, 14b may be stacked together with heating and temperature sensing sections 12, 16 and fired to a temperature of about 800° C.-1200° C. As the temperature of the stacked assembly increases, the paste may melt or soften and, when cooled, a physical or chemical bond may form joining heating section 12 to gas sensing section 14. It is contemplated that the process of applying electrodes 52 and 62, contacts 38 and 40, and/or terminal contact pads 42, 72 may alternatively be completed during the final bonding step, if desired.

The order of the particular layers of heating, gas sensing, and temperature sensing sections 12-16 may affect an accuracy of the temperature zones affected by heating elements 30, 32 and, subsequently, a gas sensing accuracy of sensing section 14. That is, based on a location of RTD 70 relative to heating element 30 and/or to first sensing component 14a, the measurement accuracy of the first temperature zone could be affected. Similarly, based on a location of RTD 68 relative to heating element 32 and/or to second sensing component 14b, the measurement accuracy of the second temperature zone could be affected. For this reason, with regard to the embodiment of FIG. 1, temperature sensing section 16 may be located immediately adjacent heating section 12. That is, heating section 12 may be sandwiched between gas sensing section 14 and temperature sensing section 16. Although FIG. 1 illustrates an embodiment where first and second sensing components 14a and 14b are positioned adjacent to one another on the same side of sensor 10, other configurations are possible. For instance, first sensing component 14a and second sensing component 14b may be positioned on opposite sides of sensor 10.

Figure 2:
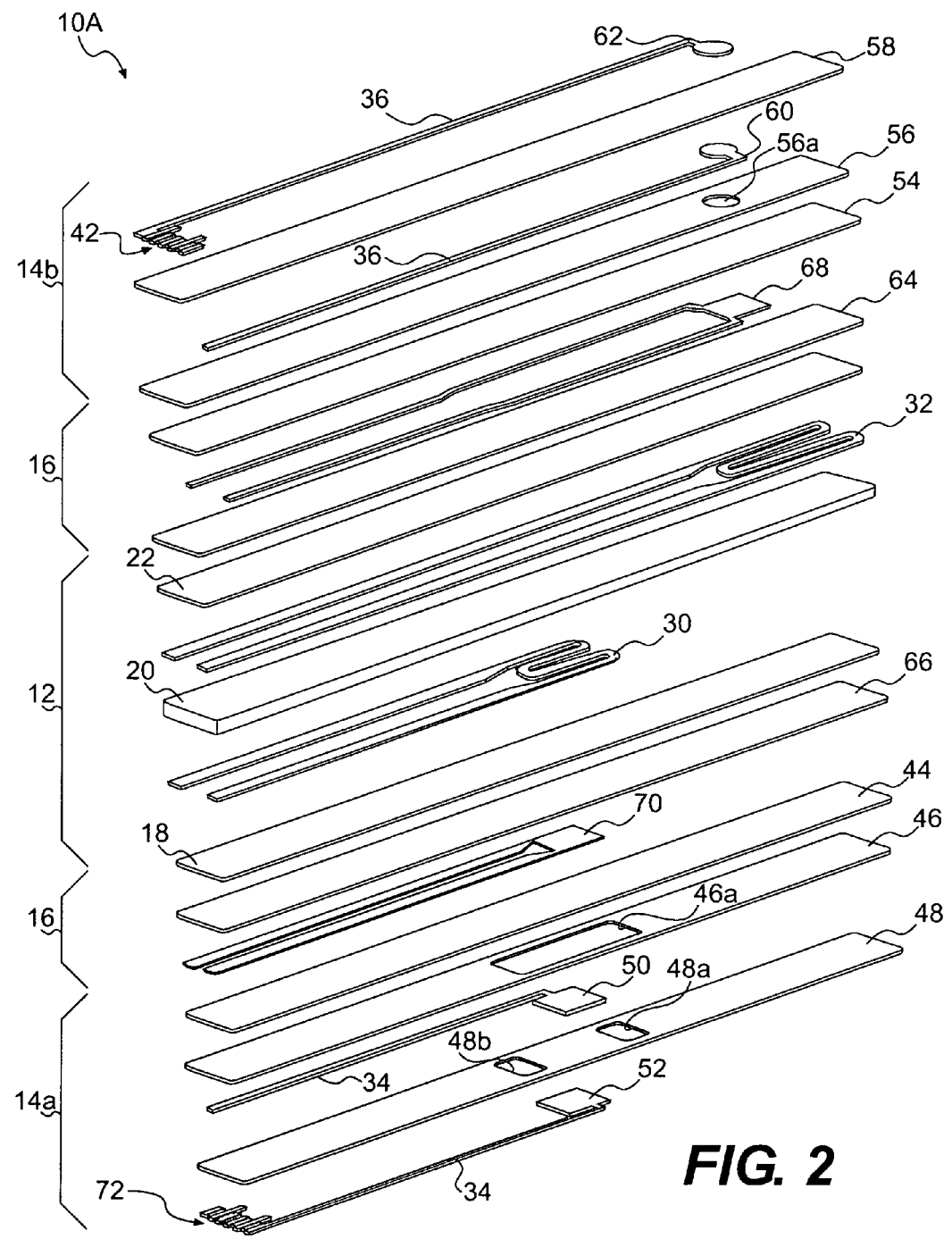
FIG. 2 is another exploded view illustration of another exemplary disclosed sensing assembly.

FIG. 2 illustrates an embodiment of sensor 10A where first and second sensing components 14a and 14b are positioned on opposite sides thereof. In the embodiment of FIG. 2, the layers (18-22, 44-48, 54-58, 64, and 66) are arranged such that heating section 12 may be positioned at the center of the multi-layer stack with both temperature sensing section 16 and sensing section 14 located on either side of heating section 12. In the embodiment of FIG. 2, one side of the sensor stack is made up of first sensing component 14a, RTD 70, and heating element 30, and the opposite side of the sensor stack is made up of second sensing component 14b, RTD 68, and heating element 32. Since RTD's 68 and 70 are each located at about the same distance from their corresponding heating and sensing elements, RTDs 68 and 70 may more accurately indicate the temperatures of the first and second heating zones. Moreover, since the sensing elements are located on opposite sides of sensor 10, the effect of one heating zone on another may be minimized. To further thermally decouple the heating zones, in some embodiments, the thickness of layer 20 may be increased. A thicker layer 20 may further improve thermal isolation between the first and second heating zones. Additionally, by extending the electrodes of first and second sensing components 14a and 14b to terminal contact pads 42 and 72, electrical leads 34, 36, and contacts 38, 40 may be eliminated in sensor 10A of FIG. 2.

In sensor 10A, the inner layers (44, 66, 18, 20, 22, 64 and 54) may be made of electrically insulating materials such as alumina or spinel, while the outer layers (58 and 48) may be primarily composed of ionically conductive materials such as YSZ. The intermediate layers (46 and 56, and possibly additional layers not shown) may be made of mixtures of the insulating material used in the inner layers and ionically conductive materials used in the outer layers, in order to facilitate a graceful transition in thermal expansion from the inner to the outer layers, and to provide good bonding between the different layers.

Similar to the layers of sensor 10, tapes of insulating (44, 66, 18, 20, 22, 64 and 54), ionically conductive (58 and 48), and intermediate (46 and 56) layers may be formed by mixing the respective material powder with binders and tape casting the resulting slurry. Devices may then be printed on the corresponding green tapes (heating elements 30, 32 and RTDs 68, 70 on the insulating layers, and electrodes 50, 60 on the ionically conductive layers), The green tape, with the heating elements, RTDs and the electrodes printed thereon, may then be stacked and laminated. The lamination may be done under heat and pressure, and may include the use of a bonding solvent. In general, the laminated part may include one or more discrete sensor pairs (such, as for instance 8 pairs of first and second sensing elements 14a, 14b), which may be singulated into individual sensor pairs. Any known separation process (such as, punching, laser machining, etc.) may be used to singulate the individual sensors. The sensing electrodes 52 and 62 may then be placed on outer layers 58 and 48 respectively, and fired at a temperature between about 600-1200° C. to cure the electrodes. As with sensor 10 of FIG. 1, instead of co-firing all the layers together, different layers of sensor 10A may also be separately sintered and joined together by bonding or other attachment processes if desired.

INDUSTRIAL APPLICABILITY

The presently disclosed sensors may be utilized to detect the presence of various gases within an exhaust flow of an engine, while maintaining a high degree of durability and accuracy. Specifically, by co-firing the RTDs with the heating section and temperature sensing section, the cost of the disclosed sensors may be reduced and the reliability and applicability increased. That is, because the RTDs may be co-fired, no additional steps (other than stacking prior to sintering) may be required to produce sensors 10 and 10A, thereby saving time and money. In addition, the bond created by co-firing may be durable, even when exposed to temperature gradients or extreme temperatures. And, because the RTDs are co-fired with the layers of the heating and/or gas sensing sections, the RTDs can be placed anywhere within the lamination. As such, the RTDs may be moved to locations that provide optimum temperature sensing accuracy.

Because the RTDs may be co-fired with the layers of heating and/or gas sensing sections, no distinct layer of bond material between the different layers may be observed. That is, the substrate layers of the heating, temperature sensing, and the gas sensing regions may be continuous and appear to have been formed as a single integral component. In contrast, if the components had not been co-fired (that is, if the components were joined by some process after separately sintering the components), a distinct bonding layer would exist between the separately formed components. In this case, sensors 10 and 10A would appear to be fabricated from multiple separate blocks of green material.

It will be apparent to those skilled in the art that various modifications and variations can be made to the disclosed sensors. Other embodiments will be apparent to those skilled in the art from consideration of the specification and practice of the disclosed sensors. For example, additional, fewer, and/or different layers than those depicted and described may be used within the disclosed sensor, if desired. It is intended that the specification and examples be considered as exemplary only, with a true scope being indicated by the following claims and their equivalents.

What is claimed is:

1. A gas sensor, comprising:
    a first ionically conductive substrate including a zirconia based material and a second ionically conductive substrate including a zirconia based material;
    a first sensing electrode and a first reference electrode coupled to opposite sides of the first ionically conductive substrate and a second sensing electrode and a second reference electrode coupled to opposite sides of the second ionically conductive substrate;
    a first electrically insulating substrate assembly including magnesium aluminate spinel, the first electrically insulating substrate assembly including a first recess and a second recess spaced apart from the first recess along an axial direction of the sensor;
    a first heating coil and a separate second heating coil coupled to the first electrically insulating substrate assembly;
    a second electrically insulating substrate assembly including magnesium aluminate spinel; and
    a first resistance temperature detector and a separate second resistance temperature detector coupled to the second electrically insulating substrate assembly, wherein:
        the first sensing electrode, the first heating coil, and the first resistance temperature detector are aligned along a first vertical axis of the sensor, and the second sensing electrode, the second heating coil, and the second resistance temperature detector are aligned along a second vertical axis of the sensor and spaced apart from the first vertical axis along the axial direction of the sensor; and
        the first ionically conductive substrate is positioned within the first recess, and the second ionically conductive substrate is positioned within the second recess.

2. The gas sensor of claim 1, wherein the ionically conductive substrate includes yttria stabilized zirconia.

3. The gas sensor of claim 1, wherein the first and second ionically conductive substrates and the first and second electrically insulating substrates are co-fired to form a single integral component.

4. The gas sensor of claim 3, wherein the first electrically insulating substrate is positioned between the ionically conductive substrate and the second electrically insulating substrate.

5. The gas sensor of claim 1, wherein coefficients of thermal expansion of the first and second ionically conductive substrates and the first and second electrically insulating substrates are within about 1 ppm/° C. of each other.

* * * * *